United States Patent [19]
Anbar

[11] Patent Number: 5,771,261
[45] Date of Patent: Jun. 23, 1998

[54] TELETHERMOMETRIC PSYCHOLOGICAL EVALUATION BY MONITORING OF CHANGES IN SKIN PERFUSION INDUCED BY THE AUTONOMIC NERVOUS SYSTEM

[76] Inventor: Michael Anbar, 145 Deer Run Rd., Amherst, N.Y. 14221-1823

[21] Appl. No.: 527,522

[22] Filed: Sep. 13, 1995

[51] Int. Cl.$^6$ .............................. G01K 13/00; A61B 5/02
[52] U.S. Cl. ............................. 374/45; 128/664; 128/736
[58] Field of Search .............................. 374/45; 128/664, 128/736

[56] References Cited

U.S. PATENT DOCUMENTS

| | | | |
|---|---|---|---|
| 4,538,617 | 9/1985 | Jensen | 128/635 |
| 4,608,990 | 9/1986 | Elings | 128/633 |
| 4,859,078 | 8/1989 | Bowman et al. | 128/736 |
| 5,507,291 | 4/1996 | Stirbl et al. | 128/745 |

FOREIGN PATENT DOCUMENTS

| | | | |
|---|---|---|---|
| 0441193 | 8/1991 | European Pat. Off. | 128/736 |
| 2203835 | 10/1988 | United Kingdom | 128/736 |

OTHER PUBLICATIONS

Quiao, Z. et al., "Simultaneous Measurement of Electrical Admittance, Blood Flow and Temperature at the Same Skin Site with a Specially Designed Probe," Med. & Biol. Eng. & Comput., vol. 25, pp. 299–304 (1987).

*Primary Examiner*—Diego F. F. Gutierrez
*Attorney, Agent, or Firm*—Hodgson, Russ, Andrews, Woods & Goodyear LLP

[57] ABSTRACT

The present invention comprises methods and apparatus for assessment of the effects mental stress involving the measurement of periodic changes in skin perfusion. Using a remotely mounted infrared camera, dynamic area telethermometry (DAT) measures the autonomic nervous activity by monitoring and quantitatively analyzing the modulation of cutaneous perfusion. When people gets "nervous" their sympathetics "act up" and they blush (vasodilates) or becomes pale (vasoconstricts). A DAT test of the face proves to be a superior "lie detector" test since emotional stress is reflected in an autonomic nervous response that can be measured remotely. DAT is much more sensitive than any visual assessment of skin color or than instrumental measurement of diaphoresis. Not only is it more reliable than currently used polygraph tests, but its non-contact administration is so simple and innocuous that it could be done without the subject's awareness. Furthermore, the same device can be used to meet the needs of a variety of psychiatric and psychological evaluation problems, including depression, drug addiction and dementia, as well as psychological learning disabilities.

8 Claims, 1 Drawing Sheet

TELETHERMOMETRIC PSYCHOLOGICAL EVALUATION BY MONITORING OF CHANGES IN SKIN PERFUSION INDUCED BY THE AUTONOMIC NERVOUS SYSTEM

TECHNICAL FIELD

The present invention relates generally to monitoring of the response of the autonomic nervous system to mental stress, involving the measurement of periodic changes in skin perfusion (with blood), which are associated with the regulation of skin temperature by the autonomic system. While this invention is related to other techniques used to measure autonomic hyperactivity such as excessive perspiration or changes heart rate, it is unique in making the measurement remotely, without physical contact with the subject, and in continuously monitoring informative physiological parameters on different exposed parts of the human body, especially on the face. The present invention has many significant differences and advantages over older autonomic nervous system tests known in the art.

BACKGROUND OF THE INVENTION

I. Prior Art and Competing Technologies

It is well known that the autonomic nervous system is affected by mental stress, resulting in changes in a number of physiological parameters. These include higher heart-rate, higher blood pressure, becoming pale or blushing, as well as exhibiting excessive perspiration (enhanced sudomotor activity); the latter is often detected by decreased galvanic skin resistance. As pointed out by Dr. Lykken in 1991, in *Integrative Physiological & Behavioral Science* 26: 214–222, by Dr. Steinbrook in 1992 in the *New England Journal of Medicine* 327:122–123, and by Dr. Furedy in 1993 in the *International Journal of Psychophysiology* 15:263–267, the classical polygraph tests based primarily on monitoring sudomotor activity are unreliable. Although computerized correlation can significantly increase the reliability of monitoring several interdependent physiological parameters, as was recently pointed out by Dr. Yankee in the *Journal of Forensic Science* 40:63–68, 1995, the use of polygraphs as "lie detectors" is still very problematic. As recently as 1994, trained interviewers have been used to overcome the shortcomings of polygraph tests, as described in the *Journal of Forensic Science* 39: 793–807, 1994. However, also this time-consuming subjective approach has a very limited reliability, as was shown by Dr. Ekman in an extensive study published in *American Psychologist* 46:913–920, 1991. The use of electroencephalography (EEG) to monitor event-related brain potentials is probably more reliable than the conventional polygraph, but it is impractical as a routine technique from the standpoints of the cost and time involved. The same is true of magnetoencephalography which can measure brain activity without contact, but only in a sophisticated, highly controlled and costly environment.

There are two types of problems with currently used "lie detectors" that severely limit their effectiveness:

1. The limitations of the devices used to gather the phychophysiological information. These include the sensitivity and precision of the measuring devices, the level of sophistication of the data analysis, the skill needed to apply these devices, the time it takes to accumulate reliable data, and the cooperation required from the subjects who undergo such a test.
2. The standardization of the mental stress, i.e., the content of questions asked, the person who asks them, and the disposition of the tested subject who is generally loaded with several attached sensors and wired to sophisticated computerized electronic systems. Even if the questioning was administered by a computer with prerecorded talk to eliminate the variance due to personality of the tester, as discussed in 1992 by Dr. Michael Anbar in the *IEEE Engineering in Medicine and Biology Magazine,* 11:57–61, there is no way, using the current technologies, to avoid the psychological effects of the attached instrumentation on the tested subject.

All those limitations are alleviated by the present invention. It is well known in neurology that modulation of skin perfusion is a much more sensitive indicator of autonomic hyperactivity than sudomotor activity. Vasoconstriction in the extremities was observed both in children and adults under mental stress or enhanced mental activity (solving arithmetic problems of serial subtraction and multiplication). However, unlike the present invention, no attempt was made in those studies to quantitatively derive the affected hemodynamic regulatory parameters. Since cardiac output periodically affects skin perfusion, the present invention can simultaneously measure the heart rate of the tested subject; heart rate is one of the other physiological parameters measured in some classical polygraph tests. Furthermore, using dynamic area telethermometry the present invention measures modulation of skin perfusion and heart rate remotely, and possibly secretively, so that unless the tested subjects are explicitly informed of the test being performed, they may not be aware of it at all.

The detection of anxiety resulting from mental stress associated with intentional deception, is just one of many problems in psychological testing that can substantially benefit from an instrument that yields an objective, quantitative measure of anxiety, manifested in autonomic hyperactivity, or of the response to standardized mental stress. These psychological or psychiatric problems include: (1) The detection and quantitative assessment of diminished responsiveness to normally stressful or exciting mental stimuli. Diminished responsiveness occurs in depression, drug addiction and dementia. Responsiveness is the manifestation of autonomic hyperactivity in response to a given mental stress or stimulus. (The difference between mental stress and mental stimuli is subjective. If the stimulus is perceived as being unpleasant it is classified as mental stress). Diminished responsiveness is the difference between the responsiveness of a tested patient and that of a group of normal subjects. (2) The detection and quantitative assessment of enhanced responsiveness or anxiety (when the stimulus is perceived as very stressful) in certain individuals exposed to stimuli that do not invoke such a response in most people. The latter situations include fear from certain creatures, objects or situations (phobias), enhanced frustration with situations that are tolerated by most people, and panic when confronted with certain tasks that most people cope with. Since anxiety is known to inhibit comprehension and judgment, as well as manual performance, the latter psychological problem is the cause of many situations of learning disability. An instrument is called for to repeatedly objectively measure the efficacy of treatment of phobias and learning disabilities, or the effectiveness of training of personnel to handle frustrating situations.

Since mental stress is often poorly perceived consciously by the individual under stress, the only way to measure its effect reliably is by its unconscious (autonomic) psychophysiologic manifestations. As stated above, the current methods to measure these manifestations (all of which involve physical contact with the tested subject), are crude and obtrusive to an extent that is likely to induce unwarranted anxiety, and thus introduce undesirable noise into the measurement. By using dynamic area telethermometry, the described invention provides the preferred means to quantitatively measure unobtrusively the psychophysiologic manifestations of anxiety.

II. Dynamic Area Telethermometry

Dynamic Area Telethermometry (DAT) is a known concept, described in a 1991 publication of Dr. Michael Anbar, *Thermology* 3(4):234–241, 1991. Further details of this technique were described by Dr. Michael Anbar in 1994 in *Medical Electronics* 146: 62–73, 1994 and 147:73–85, 1994. There is, however, no known practical application for DAT in the public domain. It is a non-invasive, functional test of the autonomic nervous system, that monitors changes in the spectral structure and spatial distribution of thermoregulatory frequencies (TRF's) over different areas of the human skin. Grounded in the science of blackbody infrared radiation as measured by infrared imaging, DAT derives information on the dynamics of bodily heat generation, transport, and dissipation from changes in the temperature distribution over skin areas of interest. Changes can be detected in the average temperatures of area segments or in the variances of those averages; the variances measure the spatial homogeneity of the temperature distribution over the given area and, therefore, the homogeneity of cutaneous perfusion; under conditions of hyperperfusion the spatial homogeneity reaches a maximum and the amplitude of its temporal modulation is at a minimum. From the periodic changes in temperature distribution over different skin areas, the thermoregulatory frequencies of the processes that control the temperature in the given areas can be derived. In addition to representing autonomic thermoregulatory function, measurable periodic changes in skin temperature also represent the heart rate and the amplitude of that change represents the cardiac output.

From the periodic changes in the spatial homogeneity of skin temperature (HST), the dynamics of the processes that control the saturation of the cutaneous capillary bed can be derived. HST is the reciprocal of the spatial coefficient of variation of temperature in small areas of skin (<100 mm$^2$): HST=average temperature divided by the standard deviation of the average temperature (HST is a dimensionless parameter). HST is determined by the structure of cutaneous vasculature and by its heat dissipatory activity. As perfusion is enhanced, more capillaries are recruited as blood conduits and HST increases. Unlike average temperature, HST is affected mainly by the behavior of the cutaneous arterioles and venules (opening or shutting of arterioles that shunt blood from the skin capillaries) and to a much lesser extent by the blood flow in subcutaneous vessels, which is controlled by vasodilation or constriction. Since the neuronal control of HST is different from that of skin temperature, HST is an independent physiological hemodynamic parameter. Like the average temperature of unit areas of skin, HST oscillates as a function of the temporal behavior of perfusion. Since the rate of increase of HST with the extent of perfusion is much larger than that of temperature, the extent of its change and the amplitude of its modulation are significantly higher than those of temperature modulation. A static image of HST is, therefore, more informative than a classical thermogram. The concept of HST has been fully described by Dr. Michael Anbar in 1994 paper published in *Biomedical Thermology* 13(4):173–187, 1994.

Quantitative DAT requires high-precision measurement of infrared flux (corresponding to <0.01° C.), low electronic and instrumental noise (<0.0005° C. equivalent of electronic or thermal noise), and long-term stability (drift of <0.1° C./hr). All these are attainable with current commercial equipment. The minimal resolution required for DAT is an image field of 128×128 pixels, which can be optically zoomed to cover an area of 10 to 10000 cm$^2$ (0.06 mm$^2$ to 0.6 cm$^2$/pixel).

To guarantee correct recognition and precise location of the anatomic features studied, it is beneficial to simultaneously generate a reflective image of exactly the same body area (to precisely record the anatomic features), and superimpose the reflective image over the emissive one to assure precise registration of any thermal abnormalities found. This concept has been fully described in a 1993 publication of Dr. Michael Anbar, *SPIE Proceedings* 2020:510–517, 1993.

DAT can be useful in the diagnosis and management of a large variety of disorders that affect neurological or vascular function. The periodicity of changes in perfusion of large regions of skin can be used to identify transient or chronic (pathological) changes in autonomic nervous function. The different clinical applications of DAT are fully described by Dr. Michael Anbar in 1994 in a monograph entitled "Quantitative and Dynamic Telethermometry in Medical Diagnosis and Management", CRC Press Inc. September, 1994. The automation of DAT, making it a fully computerized, objective testing technique, has been fully described in a 1995 publication of Dr. Michael Anbar, *SPIE Proceedings* 2473:312–322, 1995.

The simplicity, speed, non-obtrusive nature and the full automation of DAT make this technique superior to other methods of assessing the function of the autonomic nervous system, especially when the objective is to monitor autonomic hyperactivity due to mental stress. It is well known that connecting sensors to the skin (to measure sudomotor activity with impedance electrodes, skin perfusion through heat sensing with a thermistor, or neuromuscular activity through electric potential with low impedance electrodes) intrinsically poses mental stress on the tested subject, which might limit the validity of the test; moreover, all contact methods require special skill in handling and connecting the sensors to the skin. On the other hand, DAT can be used effectively even without the awareness of the tested subject, which is the ideal situation in psychological testing.

III. Areas of Application of the Present Invention

The present invention can have applications in several areas: In criminology, personnel evaluation, psychiatry, clinical psychology, and self testing for psychological behavioral assessment and feedback. In addition to be used as a "lie detector" in the interrogation of suspected criminals (including smugglers, infiltrators and spies) or prospective employees, the present invention can be used in psychiatry to evaluate levels of depression, alcoholism, drug addiction, and dementia.

The change in autonomic reaction in response to a standardized mental stimulus or mental stress (autonomic response), is the measured parameter in psychiatric applications. Autonomic response can be measured through the periodic modulation of perfusion, through the periodic modulation of skin temperature (caused by modulated perfusion), or through the periodic modulation of the spatial homogeneity of skin temperature (HST), which is caused by modulated spatial perfusion of cutaneous arterioles and venules. This invention provides an effective tool to make these measurements.

By repeatedly measuring the level of responsiveness to standardized mental stress (level of mental acuity), it can be used to determine the optimal dosage of antidepressants for individual patients. By measuring diminished responsiveness (lowered level of mental acuity), the present invention can also be used to assess the degree of addiction to opiates, as well as the effectiveness of opiate antagonists (e.g., naloxone) in individual patients.

In psychiatric assessment and management of phobias, this invention provides an effective tool to measure the level of autonomic response to the known trigger of anxiety, and then to measure the decrease in this response as a result of an appropriate desensitization treatment.

In psychological testing, the present invention can be used to assess the responsiveness to specific kinds of mental stress, which could be important in testing of students with psychological learning disabilities, as well as of employees or potential employees for their ability to cope with stressful tasks. The identification of particular learning or work situations that are excessively stressful can be key to improving the performance of students or employees. Such testing is best done in two stages: (1) Identification of the stressful stimulus or stimuli. This is a similar test to the "lie detector" test where the subject is exposed to different stimuli (e.g., learning tasks, manual mechanical tasks, or workplace situations) and anxiety associated with each of these is measured by the level of autonomic response. (2) Once the source of anxiety has been identified (which is critical in treatment of emotional learning disabilities) this invention can be used to measure the decrease in anxiety as a result of treatment, like in the case of treatment of phobias.

This invention can also be used, in parallel to video tape feedback, to improve the training of sales personnel, negotiators, teachers or orators, all of whom must cope with mental stress. It could also measure a variety of psychological parameters, such as the types of mental tasks that the subject finds more difficult or more enjoyable. These may include reading, calculating, solving different types of problems, listening to different kinds of music, different types of jokes, different kinds of visual sceneries, etc. In such psychological applications, like in the first part of a learning disability test, the goal of the test is to identify the type of mental stimulus that evokes a change in autonomic thermoregulation larger than a given threshold. Such tests can be administered completely automatically with a computer asking questions (with a standardized prerecorded voice) and the subject answering by speaking into a microphone, while a computerized infrared camera monitors the face and automatically generates the TRF spectra and analyzes them as described below.

IV. Measurements

A. Thermoregulation of skin

Skin, the largest organ of the human body, plays a major role in regulating the body's core temperature. In its heat dissipatory role, skin generally becomes warm when the body needs to dissipate excessive heat, and turns cold when the body must preserve heat. Under moderate environmental conditions, skin temperature depends primarily upon the blood flow in the vasculature close to the skin surface.

Skin temperature reflects the physiological behavior of cutaneous blood flow which is modulated by the autonomic neurological control of pertinent arteries and arterioles. Observing skin temperature at any point on the skin as a function of time can provide direct information on the neurological control of vascular function. Neurological disorders can, therefore, be associated with abnormal temporal behavior of skin temperature, in addition to changes in spatial distribution of thermoregulatory function, both of which lend themselves to quantitative assessment. Like in other neurological or neuromuscular tests, substantial diagnostic information is embedded in the dynamic behavior of the thermoregulatory system.

Although skin temperature may vary over a wide range, depending upon the environment and on the level of metabolic activity, it is regulated under normal conditions. This regulation may be occasionally less stringent, like during sleep; but even then, some skin temperature regulation is retained. Like any regulated parameter, including core temperature, skin temperature is expected to oscillate around a set point, even if the value of the set point does not remain constant. Even a simple thermostated system, such as a forced air heated and cooled house, will show temperature oscillations stemming from temperature over-shooting and delays due to imperfect thermostats and different rates of response and relaxation of the individual heating and cooling processes.

Skin temperature maintenance is due in substantial part to neuronal thermoregulation of vasoconstriction and vasodilation of the vasculature, thereby causing a characteristic modulation of skin perfusion. In a complex regulated system, such as the human body, where there are several levels of non-linear regulatory processes interacting with each other, many thermal regulatory oscillations are superimposed on each other. To deconvolute these and identify significant changes in autonomic function due to mental stress, one has to monitor the temperature of different exposed parts of the body for a certain amount of time.

B. Methods to measure periodic changes in perfusion.

As stated, DAT is the method of choice to measure modulation in skin perfusion. Microwave thermometry of the bulk tissue and thermometry of the skin using arrays of thermistors, are two alternative methods to dynamically measure temperature. Microwave thermometry has, however, a significantly lower spatial resolution (by a factor of 10,000) and lower sensitivity (by a factor of 10 to 100), which make it unsuitable to quantitatively monitor thermoregulatory oscillations of less than 0.1° C. Area thermometry by thermistors with adequate spatial resolution requires the mounting of many hundreds or even thousands of thermistors all over the skin, which is a prohibitively cumbersome process. Liquid crystal contact thermography (LCCT) has too low precision (>0.5° C.) and too long response time to be useful in quantitative dynamic measurements.

Other methods of continuously measuring the modulation of skin perfusion include ultrasound (measuring changes in ultrasonic impedance, because the speed of sound is temperature dependent and because of changes in the average density of hyperperfused tissue, or by measuring changes in the average velocity of erythrocytes by Doppler shift). Ultrasonic measurement of perfusion cannot be done simultaneously on many areas. In addition to requiring repeated change changes of physical contact, which, by itself, may induce mental stress as well as local neurological response, it also requires a highly skilled technician to measure the changes in perfusion in different areas. Moreover, using ultrasound it is necessary to apply a coupling lotion in order to make contact between the ultrasonic probe and the skin. The application of such coupling lotion and the contact of the ultrasonic probe may alter local perfusion by affecting thermal and tactile neuronal sensors.

Another method of measuring modulation in skin perfusion is infrared Doppler velocimetry (IRDV), which measures the Doppler shift of the near infrared radiation (about 1 $\mu$m) reflected from erythrocytes. IRDV, however, cannot monitor modulation of perfusion over large areas of skin in a reasonable time (it might take several hours to accumulate the same information on the temporal behavior of skin perfusion that can be measured in less than 3 minutes by DAT).

Another method of measuring modulation in skin perfusion is impedance plethysmography (because the ionic conductivity of tissue depends on the amount of plasma between the electrodes). This method, which requires the mounting of an array of electrodes on the skin by a skilled technician before any measurement can be done (which makes it substantially more expensive), is also less sensitive to minute oscillations, and its spatial resolution (limited by the number of electrodes used) is significantly lower than achieved by DAT.

Other methods for continuously measuring the modulation of skin perfusion, such as magnetic resonance imaging or single photon emission tomography, are utterly impractical as psychological testing methods.

DETAILED DESCRIPTION OF THE PREFERRED EMBODIMENTS

Figure 1A:
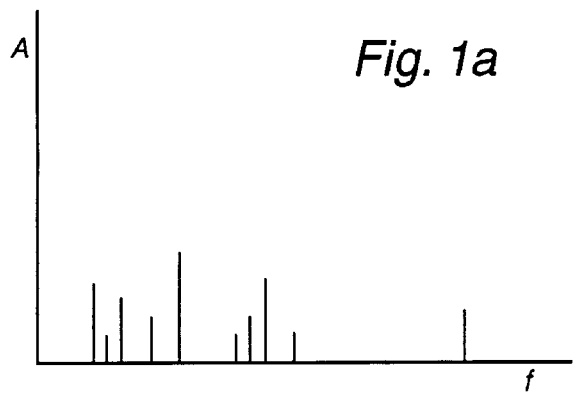

The monitoring technique measures the changes in the temporal behavior of cutaneous perfusion caused by mental stress. These changes, which are manifested by related changes in skin temperature, can be observed anywhere on exposed skin, best represented by the face.

The face of a subject is observed by a computerized infrared camera which continuously monitors the periodic modulation of temperature of the face's skin, which is controlled by autonomic neuronal modulation of skin perfusion. The output of the computerized camera can provide 5 independent measures of autonomic nervous activity. (1) The periodic modulation of skin perfusion generates temperature oscillations, from which neuronal thermoregulatory frequency (TRF) spectrum can be derived. When the subject is questioned by a person, by a tape recorded message, or by computer controlled digitized prerecorded talk, and the question exerts mental stress, changes occur in the TRF spectrum in frequency and/or amplitude. The same is true when the subject observes a video movie with emotionally exciting scenes. The extent of change substantially increases when the verbal or visual input induce excessive mental stress on the subject, resulting in autonomic hyperactivity. (2) Like skin temperature, also HST changes as a result of the autonomic neuronal modulation of cutaneous perfusion (changing the shunting of arterioles). Consequently, the frequencies of HST modulation are an independent measure of the effect of mental stress. (3) The frequency in the TRF spectrum of temperature that represents the heartbeat may also increase at the same time, corroborating autonomic hyperactivity. (4) Another independent autonomic neurological parameter that can be extracted from the image of face, is the rate and regularity of blinking of the eyes; like heartbeat this is an involuntary neuromuscular activity. (5) In addition, because of the innervation of the autonomic sympathetic and parasympathetic subsystems, the temperature variation on different parts of the face differ depending on the degree of mental stress. This constitutes a fifth measure of mental stress.

In the lie detector testing mode, the extent of change in each of the first four parameters following each verbal input is registered, and the combined difference in response to a set of neutral versus relevant questions (or statements) in the given dialog, is used to measure the degree of intentional deception, generally associated with autonomic hyperactivity. As described below, other psychological or psychiatric tests do not use the heart rate or the rate of blinking as measures of anxiety.

The neuronal and hemodynamic (heartbeat) oscillations are measured by fast Fourier transform (FFT) analysis, an analysis method well known in the art of the temporal behavior of skin perfusion (manifested in the dynamics of skin temperature and of HST).

As discussed above, modulation of skin perfusion can be continuously measured by several techniques. Because of its sensitivity, fast response time, speed of data acquisition and low cost, DAT is the preferred method of measuring periodic modulation of perfusion of the skin and identifying psychophysiologic effects. It possesses a sensitivity of up to 0.001° C. (i.e., about 50 times smaller than the level of temperature modulation under normal physiological conditions). DAT allows for the accumulation of hundreds of sequential thermal images that are then subjected to FFT analysis to extract the frequencies and amplitudes of periodic temperature changes at each pixel, or group of pixels, of the image.

The underlying frequencies of HST oscillations are derived from the same DAT data, using the same computational technique, only that in this case the measured parameter used in the calculation is the spatial variance of temperature. To measure the HST, the image is subdivided into a matrix of small areas, each corresponding to say, 64 mm$^2$ of skin, and the temperature values of the pixels in each such subarea of the image are averaged. The variance of the average temperature is used to calculate the HST of each subarea. The HST values of all the accumulated images are then analyzed by FFT to extract the frequencies and the corresponding amplitudes of the periodic modulation of skin perfusion.

DAT requires a highly stable, high resolution, highly sensitive, computerized infrared camera, preferably operating in the 8 to 14 $\mu$m range (the use of cameras in the 3 to 5 $\mu$m range, often used for surveillance, is less desirable because of the substantial reflectivity of human skin in that region of the infrared spectrum). To meet the specific DAT needs, it is preferred that the camera's computer be programmed to quantitatively analyze the temporal behavior of many thermal images with a sufficient resolution (e.g., 256×256 pixels). While successful results can be achieved by analyzing the temporal behavior of at least 64 thermal images, it is preferred to measure 256 or 512 thermal images. Since in DAT psychological testing, each dynamic measurement series must be complete in 10 seconds, the question-answer time used in a natural dialog, the rate of data acquisition must be at least 30 frames per second, which is well within the state of the art of commercial infrared cameras.

The thermal images are temporarily stored in random-access memory (RAM) using an appropriate compression scheme, because one needs the data of all the images to perform the FFT on the time series of temperature values of each pixel or subarea before the next question is posed. With a 40% compression, each time series of 256 images requires a memory of less than 20 megabytes, which can be readily installed in any modern desktop computer. The FFT yields the frequency spectra of each pixel together with the relative or absolute amplitude of each TRF.

The heartbeat frequency can be identified separately by its characteristic blur (lack of exact periodicity) in the FFT spectrum within the frequency range of 900 to 2000 mHz. The sum of the amplitudes of the frequencies within that blurred band are summed up and tabulated as a single amplitude of the median frequency within that band.

The software can then tabulate the spatial distribution of the TRF's with amplitudes above a given threshold (e.g., frequencies with amplitudes larger than 1% of the total thermal modulation). Once the TRF's with amplitudes above that given threshold are tabulated, they are rank ordered, and a subset of frequencies above a certain cutoff value (e.g., the frequencies with the 10 largest amplitudes) are selected and defined as the prominent frequencies. The same procedure is followed with the HST data. However, the display of the spatial distribution of the prominent TRFs, which is being used in other applications of DAT, is not necessary to meet the needs of psychological testing.

Figure 1B:
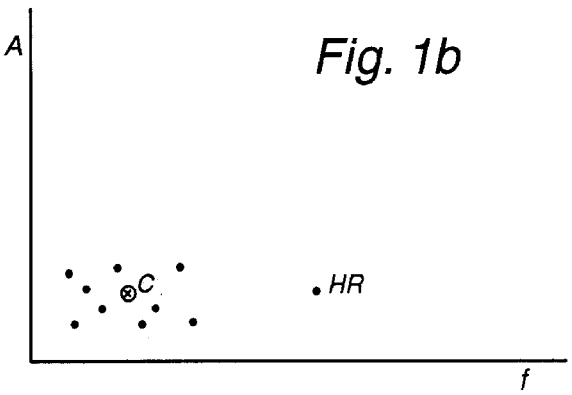
Figure 1C:
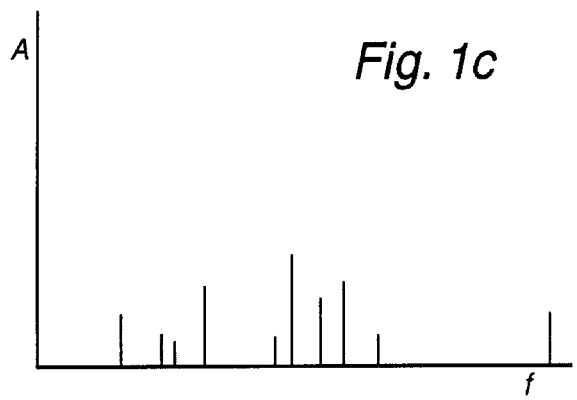
Figure 1D:
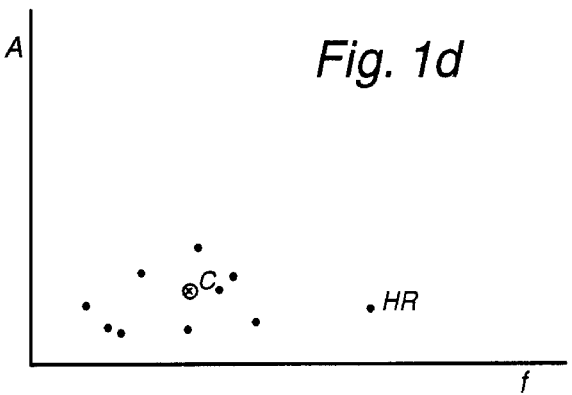
Figure 1E:
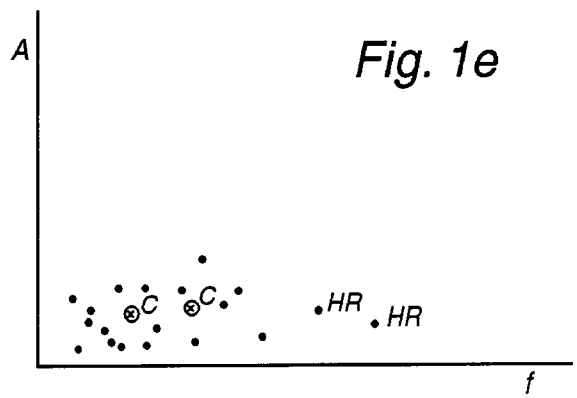

The discriminant analysis that determines the identity or difference between different thermoregulatory FFT spectra, associated with different levels of autonomic activity induced by mental stress, uses cluster analysis. In cluster analysis, which is well known in the art, each frequency-amplitude pair of a FFT spectrum is represented by a dot on a plane that is described by amplitude versus frequency coordinates. As shown in FIG. 1a, a FFT spectrum of the frequencies with the 10 prominent amplitudes is represented in FIG. 1b by a cluster of 10 points on the frequency-amplitude plane. The geometric center of this cluster (C) is also marked in this figure (a geometric center can be looked upon as the center of gravity of planar sheet defined by the boundaries of the cluster). The center of this cluster of TRF's does not include the frequency that represents the heart rate (marked as HR on the figure). A different FFT spectrum (FIG. 1c) is represented by a different cluster on the same plane (FIG. 1d). The two clusters may partially overlap, as shown in FIG. 1e, and a mathematical procedure, well known in the art, can determine the level of significance of the difference between the two spectra, represented by the extent of overlap of the two clusters. A common measure of the difference between two clusters is the calculated probability (p) that the two clusters compared are actually members of a single cluster, i.e., that statistically there is no difference between those two clusters. It is generally accepted that if p is smaller than 0.05 (i.e., that there is less than a 5% chance that the two clusters are identical) the difference between the two clusters is statistically significant.

Figure 1F:
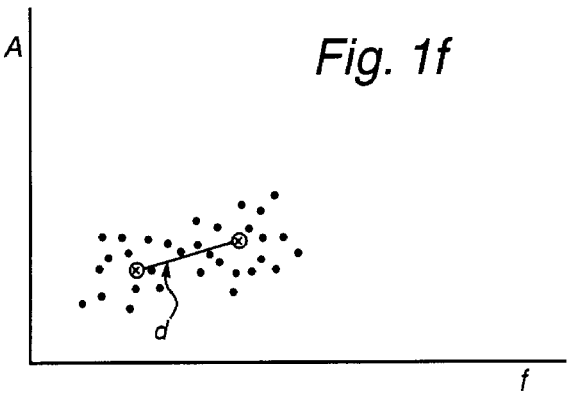

The same procedure can be repeated for many FFT spectra to determine if they represent a single group or multiple groups of different spectra. As shown in FIG. 1f, the distance (d) between the centers of the two clusters or groups of clusters on the amplitude-frequency plane is a measure of the level of difference between the two groups of FFT spectra. It is noteworthy that d and p are independent measures—there may be a substantial distance between the geometric centers of two clusters but the difference between them may still not be statistically significant. Therefore, d is a meaningful measure of the level of difference between clusters only if p is sufficiently small. The distance d is more informative than the p value as a measure of difference between clusters. For instance, any two out of three clusters, A, B and C, can be different from each other at the same level of significance, say 0.01, but the distance between cluster B and cluster A (the reference unstressed situation) can be significantly larger than between clusters C and A. Since the distance d is a measure of responsiveness, we conclude that the responsiveness to exposure to mental stimulus B is significantly larger than following exposure to mental stimulus C.

Although FIGS. 1a to 1f referred to the statistical handling of FFT of temperature modulation, they are equally pertinent to the statistical handling of FFT of perfusion, which causes the temperature modulation, and to the statistical handling of FFT of HST which manifests the spatial modulation of perfusion of cutaneous arterioles and venules.

The infrared camera can be equipped also with video CCD (or, in a scanning camera, with a photodiode detector), to produce a reflective (visual) image of the subject's face. The visual image is then recorded on a video tape, or digitally stored on a disk, for future reference. This may be needed for interrogating systems that are fully computerized, such as a routine check in into a high security area, or an automated customs checkout, where a photographic record of the tested subject may be needed.

The following steps must be taken to identify a dishonest subject (a liar), i.e., someone who intentionally makes untrue or misleading statements:

1. The subject is seated in front of a computer which asks pertinent prerecorded questions while a computerized infrared camera focuses on the subject's face. The subject may or may not be aware of the camera, which converts an image of infrared flux (256×256 pixels) into a thermal image where each pixel has a certain temperature value. The subject answers into a voice sensitive microphone without recorder (since the answers are not relevant to this mental stress test) or, if desired, into a microphone connected to a tape recorder. The camera records the thermal image of the face each time the microphone is activated following a question, at a rate of 30 images per second, and stops recording once a number of images sufficient for an effective FFT (e.g., 256 or 512) have been accumulated and stored (using data compression if needed).

2. Using a rudimentary pattern recognition program, the computer identifies the nose, which is always colder than the rest of the face because of the repeated intake of the relatively colder ambient air, and the two upper eye lids proximal to the nose, which are always warmer than the rest of the face (these are minimally affected by mental stress because of the proximity of the large supratrochlear artery to the skin; compared with cutaneous arterioles, large arteries undergo limited autonomic vasoconstriction), and uses them as anatomical markers.

3. Using similar software to that is used in military homing or targeting devices, the computer uses the anatomical markers to align all the accumulated images. This is necessary to compensate for movements of the subject's face during each test interval of data acquisition (about 10 seconds).

4. The computer then marks 6 areas, 200 mm$^2$ each, on the face: 3 on the forehead (one above the midline of the nose and 2 above both eyes equidistant from the one in the center),2 on the two cheeks (equidistant from the midline of the nose), and one on the chin. In addition, it marks the eyeballs which are monitored for the rate of blinking. It then calculates and stores the average temperature value and standard deviation of the pixels within each of the 6 marked areas on each of the 256 or 512 images. The stored temperatures and standard deviations constitute 12 time series of that test interval (a test interval is the 10 seconds following the end of each external verbal input in the dialog).

5. The temperature values of the eyeballs is averaged and used to pick up and count instances (represented by a short series of images) when these values change abruptly, indicating a blink. The computer then registers the number of blinks in each test interval. Normally, in the absence of autonomic hyperactivity, not more than 2 blinks are expected within a test interval. More than 4 blinks in 10 seconds is generally a significant indicator of anxiety.

6. The computer then subjects each of the 12 time series to FFT analysis, extracts the contributing frequencies and their relative amplitudes, and stores the FFT spectrum of each time series on a hard disk. Steps 2 through 6 take place during the interval (about 10 seconds) while the computer asks the next prerecorded question.

7. The computer picks the FFT spectrum of each time series, rank orders the amplitudes, and selects the frequencies with the 10 highest amplitudes in each series, plus the heartbeat frequency. It then stores the frequencies and amplitudes of the subset of frequencies that have prominent amplitudes.

8. The computer then performs a two-dimensional cluster analysis classification of amplitude and frequency of the spectra of prominent temperature amplitudes of each of the selected areas on the face, for all the test intervals of the dialog (e.g., 20 test intervals are accumulated in a 5 minute dialog).

9. The computer then compares for each of the selected areas the clusters with the neutral (not intended to invoke enhanced autonomic response) versus relevant (potentially exciting, resulting in autonomic hyperactivity) questions in the dialog; this is easy when the dialog is conducted with digitally prerecorded questions, which allows exact synchronization between the question and the psychophysiologic response. The computer determines the probability p that the frequency-amplitude clusters represent a single group of spectra. If p>0.05, chances are that the tested subject is probably dishonest, but the final outcome of this test is pending the following steps in the calculation. The computer also calculates the distance on the frequency-amplitude plane between the centers of the two groups of clusters.

10. Steps 7 to 9 are repeated for each of the 6 areas and the geometric average of p is calculated. $p_{av}^2 = (p_1^2 + p_2^2 + \ldots + p_6^2)/6$. The geometric average is used because the p values in the different areas are not independent of each other.

11. Steps 7 to 10 are repeated for the HST data.

12. The combined $1-p_{FFT}$ value for $p_{av}$ of Steps 10 and 11 is calculated: $(1-p_{FFT})=(1-p_{av(10)})(1-p_{av(11)})$. This calculation is justified because skin temperature and HST are independent parameters. If the $1-p_{FFT}$ value is lower than 0.90, the subject is probably not truthful, but the final outcome of this test is pending the next two steps in the calculation.

13. The computer extracts the frequency of heartbeat (which are equal to the heart rate) for each of the test intervals and using the conventional Gosset t test for two-sample of correlated data for the neutral versus relevant questions, determine the t value from the means and standard deviations of the heart beat rate following the two types of questions. If, for instance, the t value for a set of 10 neutral and 10 relevant questions, presented at random, is larger than 3.24, then the level of significance $p_{HR}$ is smaller than 0.01, i.e., there is a over 99% probability that the subject is dishonest. If, taking the same example, the t value is smaller than 1.38 than $p_{HR}>0.2$, i.e., there is a chance of more than 20% that by the criteria of this parameter the subject is truthful, i.e., there is too little statistical indication that the subject is dishonest.

14. Procedure 13 is repeated with the number of eye blinks in the different test intervals, calculating $P_{BR}$.

15. The computer calculates $1-p_{inm}=(1-p_{HR})(1-p_{BR})$ (inm stands for intermittent neuromuscular parameters). Then it calculates the overall probability $p_{OA}$ of error given all the probability values obtained in procedures 12 to 14, which is the probability that the tested subject is falsely marked as a "liar". $1-p_{OA}=(1-p_{FFT})(1-p_{inm})$ The value of $P_{OA}$ is the ultimate output of the "lie detector" test. If $p_{OA}$ is smaller than 0.2, which would be the case if any one of four parameters has p>0.05 and the other three had p=0.05, the test would statistically indicate that the tested subject is dishonest.

The psychological testing modality differs in certain aspects from the "lie detector" modality. The "lie detector" measures the probability that the tested individual is dishonest by detecting excessive mental stress in response to certain relevant or "sensitive" questions, which would sound neutral to a truthful subject. On the other hand, the psychological test measures the level of perceived mental stress through its effect on autonomic activity. While in the former modality we tried to identify instances when a certain seemingly unexciting input invokes anxiety in a dishonest subject, in the psychological testing modality we measure the extent of autonomic response (generally, hyperactivity) caused by a stressful or exciting input. This test is intended, on one hand, to identify and stage individuals who remain unusually less different to stress that would cause normal subjects to react with a significantly enhanced autonomic response. Staging implies assessment of the degree of abnormal behavior compared with normal behavior. On the other hand, this test measures unusually strong autonomic responses in certain subjects who overreact when confronted with specific kinds of mentally stressful situations.

As stated, the gist of the psychological testing modality is to measure the level of autonomic response when the tested subject is stimulated with a standardized mental stress and/or frustration. The level of autonomic response is the extent of change in autonomic thermoregulatory control measured by the distance d on the frequency-amplitude plane when p<0.05. Standardized mental stress and/or frustration are mental stimuli that were proven on a large population of normal subjects to invoke a sizable level of autonomic hyperactivity or responsiveness. One can then tabulate the responsiveness to a set of common mental stress stimuli, and use these in testing the behavior of patients or other subjects.

Mental stress can be exerted in a large variety of ways; here are some examples: Mentally solving non-rivial arithmetic problems. Solving a difficult or an absurd word puzzle. Pushing a button when one sees on a computer screen two specific geometric forms (e.g., two pentagons) with two specific colors (e.g., red and green) and the expected correct signal appears just once, at the beginning of the test, followed by a long series of similar and confusing distracters; each time the button is pushed wrongly an exceptionally annoying buzz sounds. Being asked to spell some difficult words and being shown at random a green light signal for "right" and a nasty buzz for "wrong". Having to accomplish a computer-game task, e.g., shooting down an airplane within an impractically short time. Being asked to memorize and repeat (or punch in) a sequences of numbers that grow longer beyond normal memorization capacity while being given randomized signals of "correct" or "incorrect". Being shown a video movie with unexpected frightening scenes, with suspense loaded music unrelated to a pastoral scene, with someone suddenly screaming at the observer for no known reason, etc. In brief, DAT measures the level anxiety invoked by an input that was standardized by testing a population of normal subjects.

Unlike in the "lie detector" test mode, in the psychological tests the subject is fully aware of the test, and the face can be held steady by positioning the chin on an ophthalmologic chin rest, alleviating the need for step 3 in the "lie detector" procedure. This test also permits the evaluation of many more subareas on the face that can yield pertinent information on the autonomic nervous function. This is especially important when one wishes to establish the threshold of mental stimuli needed to evoke a significant autonomic response. Since this test is quantitative in nature, it does not include the heartbeat or eye blinking parameters which do not provide sufficient information for a quantitative evaluation of the extent of autonomic response, i.e., the level of anxiety. The entire psychological test may take 15 minutes or longer:

1. The tested subject is seated in front of a computer with the chin on a chin rest. The computer provides prerecorded verbal output, computer graphics or brief scenes of a digitized video movie. The camera is mounted above the computer focusing on the subject's face. Like in the "lie detector" modality, the computerized camera converts an image of infrared flux (256×256 pixels) into a thermal image, where each pixel has a certain temperature value. The subject answers into a voice sensitive microphone without recorder (since the answers are not relevant to this mental stress test) or, if desired, into a microphone connected to a tape recorder. However, unlike in the "lie detector" modality, the camera records the thermal image of the face continuously at a rate of 60 to 100 images per second, but stops recording once a number of images sufficient for an effective FFT (e.g., 256 or 512) have been accumulated and stored (using data compression if needed) on an optical disk for subsequent analysis. Steps 2 through 10 are done after the data accumulation for the whole psychological test is complete. Steps 2 through 10 take less than 5 minutes to complete.

2. The image of the face is subdivided into about 100 subareas and a time series of average temperature and HST is produced for each test interval of 5 to 6 seconds (256 or 512 images).

3. FFT analysis is performed on the temperature and HST values for each of these time series of each of the subareas, similarly to steps 5 and 6 in the "lie detector" procedure, and the FFT spectra of the prominent frequencies are stored for further analysis. Each test interval is assigned a sequential number (from 1 to say, 200, if the whole test took 1000 seconds, or about 16 minutes). Those consecutive numbers represent units on a time axis along which changes in autonomic activity are measured under intermittent standardized mental stress.

4. Changes in autonomic activity of a given subarea are followed by cluster analysis in the amplitude-frequency domain of the FFT spectra of consecutive test intervals. The FFT frequency-amplitude spectrum of a test interval for a given subarea is added as a cluster to the cluster of the preceding test interval. If the two clusters overlap, the computer averages the FFT spectra of the two test intervals and uses it in the analysis of the spectrum of the subsequent test interval. If the clusters of subsequent FFT spectra do not overlap, no averaging is done and the subsequent FFT spectra are added one by one as dots on the plane that describes the amplitude-frequency domain.

5. A significant change in autonomic behavior is manifested by the formation of a new, significantly different cluster, implying the appearance of new frequencies with prominent amplitudes, or of a substantial change in the relative amplitudes of the current frequencies.

6. The appearance of a new group of spectra in the cluster analysis is correlated with the exposure to mental stress along the time axis of the test. If a positive correlation is noted ($p<0.05$), the level of difference (represented by the distance between the centers of the said clusters, each representing a separate group of FFT spectra) is a measure of the level of autonomic hyperactivity (change in autonomic behavior) to a given standardized mental stimulus.

7. If two or more different kinds of mental stimuli are used in a single test, the computer calculated the level of significance and distance between the groups of FFT spectra associated with those different kinds of mental stimuli.

8. Procedures 4–7 are repeated with each subarea of the image.

9. The computer rank orders the subareas according to the level of significance of autonomic response to mental stimuli, selects the 20 most significant subareas and averages the levels of significance p and the distances d of those as a final measure of responsiveness to a given mental stimulus.

10. If more than one kind of mental stress was used in a test, procedure 9 is repeated for the distances from the reference cluster in response to each of the different kinds of mental stress.

11. The computer calculates the quotient $q_d$ of the measured average distance on the frequency-amplitude plane due to a given mental stress or mental stimulus, divided by the average distance obtained with the same stimulus or stress in a standardized test on a normal population. Since two q values are obtained: one for the temperature and one for the HST data, the eventual output of the psychological test is $q_{dav}$, the average of those two q values. The $1-q_{dav}$ is a measure of diminished responsiveness. When the test is used in clinical management or in training, the output of this test is the quotient $q_m$ of the distances before and after that stage in treatment or training. The eventual output is then $q_{mva}$. When the treatment or training are aimed at controlling anxiety, the aim is to minimize $q_{mav}-1$. When the treatment or training are aimed at controlling depression, addiction or dementia, the aim is to minimize $1-q_{mav}$.

Since depression, alcoholism, drug addiction and dementia are associated with subdued autonomic response to mental stimuli, the parameters produced by procedure 11 can be used to assess the severity of the condition and help in its management so as to increase responsiveness (minimizing $1-q_{mav}$). For instance, using this test one can determine the level of medication that can revert the level of autonomic response to normal, or at least significantly improve it. Procedure 11 can also be used to objectively determine the sensitivity to frustration of personnel that might have to function under frustrating conditions, and to determine the efficacy of training to cope with frustrating situations (minimizing $q_{mav}-1$). Procedure 10, which measures the difference between responses to different forms of mental stress or mental stimuli, can be especially helpful in assessing the fitness of an individual for a specific profession or task, as part of a complete psychotechnical evaluation.

Although the description of the test is limited to monitoring the temporal behavior of temperature on the face, since the face is the most readily exposed part of the body.

However, the same procedures are applicable to the hands, arms, feet, legs, neck or any other exposed part of the body. Actually, in certain psychological test situations it may be advantageous to monitor the hands or the arms.

Although the invention has been described in detail for the purpose of illustration, it is to be understood that such detail is solely for that purpose and that variations can be made therein by those skilled in the art without departing from the spirit and scope of the invention except as it may be limited by the claims.

I claim:

1. A non-contact method for detecting a response involving the autonomic nervous system caused by mental stress in humans comprising the steps of:
   a) providing a means for measuring changes in periodic modulation of skin perfusion;
   b) measuring said changes in periodic modulation of skin perfusion;
   c) providing a means for detecting statistically significant changes in periodic modulation of skin perfusion;
   d) detecting said statistically significant changes in periodic modulation of skin perfusion; and
   e) identifying as a said response, each occurrence of said statistically significant changes in periodic modulation of skin perfusion.

2. A method according to claim 1 wherein said means for measuring said changes in periodic modulation of skin perfusion is a computerized infrared camera.

3. A method according to claim 1 wherein said changes in periodic modulation of skin perfusion are measured by measuring changes in periodic modulation of skin temperature.

4. A method according to claim 1 wherein said changes in periodic modulation of skin perfusion are measured by measuring changes in periodic modulation of spatial homogeneity of skin temperature.

5. A method according to claim 1 wherein said mental stress is associated with a dishonest statement by said humans.

6. A method according to claim 5 wherein said changes in periodic modulation of skin perfusion are measured by measuring changes in periodic modulation of skin temperature.

7. A method according to claim 5 wherein said changes in periodic modulation of skin perfusion are measured by measuring changes in periodic modulation of spatial homogeneity of skin temperature.

8. A method according to claim 1 wherein said response is diminished.

* * * * *